United States Patent [19]
Tamura et al.

[11] 4,442,355
[45] Apr. 10, 1984

[54] DEVICE FOR DETECTING SECONDARY ELECTRONS IN A SCANNING ELECTRON MICROSCOPE

[75] Inventors: Nobuaki Tamura; Susumu Takashima, both of Akishimashi, Japan

[73] Assignee: Jeol, Ltd., Tokyo, Japan

[21] Appl. No.: 286,056

[22] Filed: Jul. 22, 1981

[30] Foreign Application Priority Data

Jul. 31, 1980 [JP] Japan ................. 55-105516

[51] Int. Cl.³ .............................. H01J 37/26
[52] U.S. Cl. ..................... 250/310; 250/397
[58] Field of Search ............... 250/310, 397

[56] References Cited

U.S. PATENT DOCUMENTS 3,474,245 10/1969 Kimura et al. ............... 250/397
3,694,652 9/1972 Banburg ...................... 250/310
3,760,180 9/1973 Weber ......................... 250/310
3,896,308 7/1975 Venables et al. ............. 250/44310

Primary Examiner—Bruce C. Anderson
Attorney, Agent, or Firm—Webb, Burden, Robinson & Webb

[57] ABSTRACT

In one type of scanning electron microscope, a specimen is inserted substantially centrally in a gap between the magnetic pole pieces of an objective lens and the secondary electrons from the specimen are detected by the detecting means disposed upwardly of the objective lens. In this invention, a pipe electrode is incorporated along the optical axis of the objective lens between the objective lens and the detecting means so that the primary electron beam irradiating the specimen is not adversely affected by the detecting means. Further, a mesh electrode maintained at positive potential against the specimen is incorporated at the bottom end of the pipe electrode so that almost all the secondary electrons from the specimen are attracted toward the detecting means.

6 Claims, 3 Drawing Figures

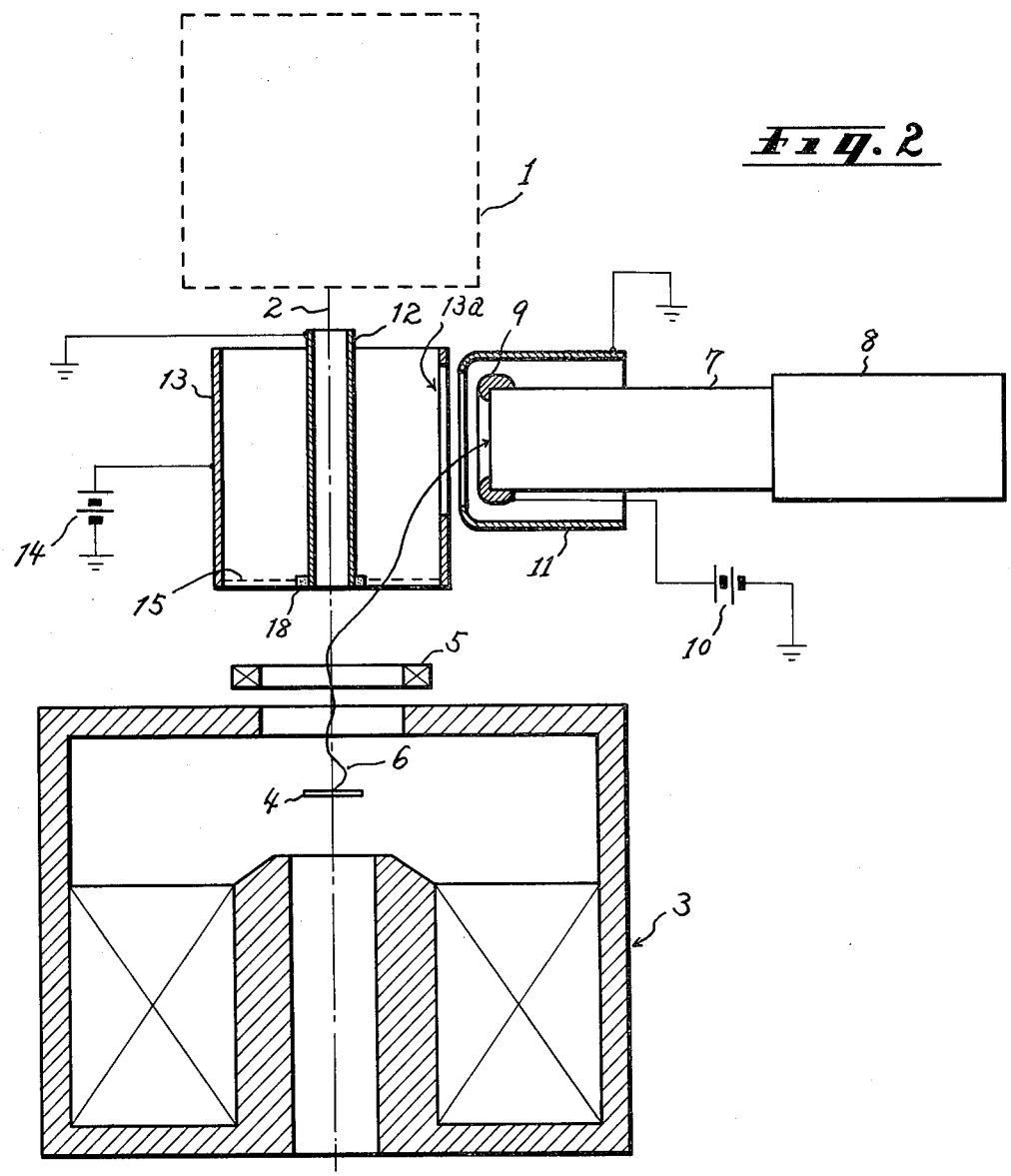
_fig. 2_
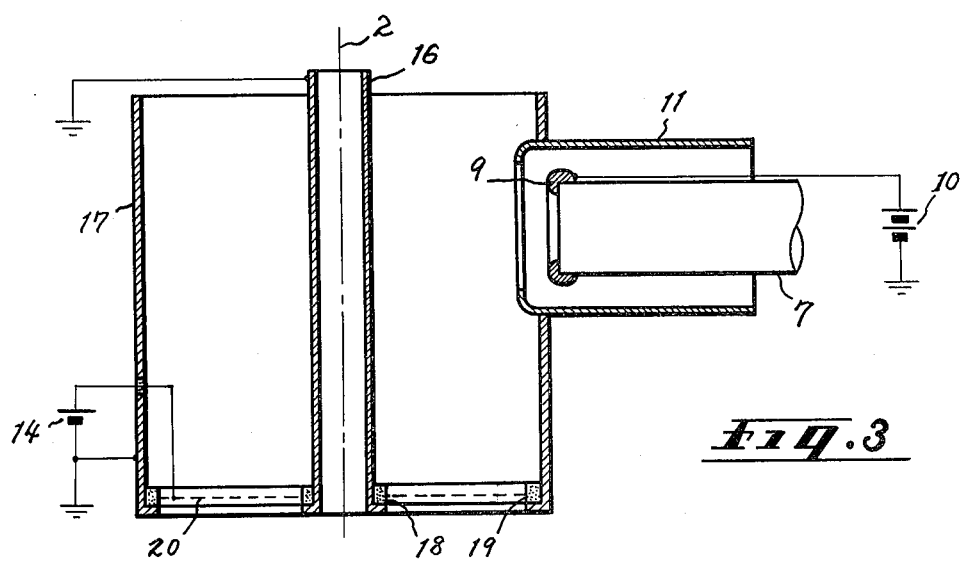
_fig. 3_

DEVICE FOR DETECTING SECONDARY ELECTRONS IN A SCANNING ELECTRON MICROSCOPE

BACKGROUND

The present invention relates to an improvement in a device for detecting secondary electrons from a specimen in a scanning electron microscope.

Recent transmission type electron microscopes are equipped with an additional device allowing observation of the scanning microscope image with secondary electrons. With such a modified scanning electron microscope, it is customary for the specimen to remain inserted in a gap between the magnetic pole pieces of an objective lens when observing the scanning image, as it was when observing a transmitted microscope image. An example of such a combination of prior art is illustrated in FIG. 1, in which designated at 1 is a system for illuminating a specimen with an electron beam, the system comprising an electron gun for producing the primary electron beam along an optical axis 2 and a condenser lens for converging the electron beam. The specimen 4 is inserted substantially centrally in a gap between the magnetic pole pieces of an objective lens 3. The electron beam for illuminating the specimen along the optical axis is focused on the specimen surface by a magnetic field generated in front of (toward the electron gun) the specimen. The objective lens magnetic field in front of the specimen thus acts as a final stage condenser lens, and also acts as the deflecting means together with a deflection coil 5 disposed above the upper magnetic pole piece of the object lens so that the electron beam scans two-dimensionally over a surface of the specimen, and further acts as the focusing means for focusing secondary electrons 6 emitted in all directions from the specimen surface toward the direction of the optical axis. A device for detecting the secondary electrons is disposed upwardly of the objective lens, and comprises a light pipe 7 with a scintillator attached to a front (toward optical axis) end thereof, a photomultiplier 8 positioned at the rear end of the light pipe, and others. The scintillator on the front end of the light pipe 7 is coated on its front (toward optical axis) face with a thin conductive layer. Such conductive layer and an accelerating ring electrode 9 therearound are held at a potential of the order of +10 KV by a d.c. power supply 10. A shield sleeve 11 which is at a ground potential is disposed in surrounding relation to the front end of the light pipe.

With the arrangement shown in FIG. 1, the secondary electrons emitted from the specimen 4 have relatively low energy ranging from several eV to several tens of eV, and hence become focused progressively in the direction of the optical axis 2 as the secondary electrons follow a spiral path. The secondary electrons tend to divert from the optical axis 2 again as they move out of the magnetic field formed by the objective magnetic pole pieces. The ring electrode 9, however, forms an electric field which extends above the objective lens and serves to accelerate the secondary electrons toward the scintillator. The secondary electrons as they hit the scintillator generate light, which is transmitted through the pipe 7 and converted by the photomultiplier 8 into electrical signals to be picked up. Since the primary electron beam which is focused onto the specimen has relatively high energy that is normally 20 KeV or higher, the degree to which the electron beam is deflected by the ring electrode 9 is negligibly small.

SUMMARY OF THE INVENTION

It is preferred that the primary electron beam irradiating the specimen should have high energy so that it transmits through the specimen with an increased power of transmission. However, producing a scanning image with secondary electrons does not of necessity require such a high energy, and instead there are some instances where an electron beam with low energy is preferred to prevent the specimen from being damaged by electron beam irradiation. In such a case, primary electron beam is used which is accelerated by low voltage, for example, by several KV and the magnetic field of the objective lens is set at low excitation. However, such low energy electron beam is then adversely affected or deflected largely by the electric field generated by the ring accelerating electrode 9, and secondary electrons are not sufficiently collected by the weak magnetic field intensity of the objective lens. As a result, high quality scanning microscope image is not obtained.

The main object of the invention is to provide a device for obtaining a secondary electron signal with sufficient intensity under the condition that low energy electron beam irradiates the specimen positioned in the weak magnetic field of the objective lens.

Another object of the invention is to provide a device in which the electric field generated for accelerating the secondary electrons emitted from the specimen cannot deflect the low energy primary electron beam irradiating the specimen.

According to this invention, the low energy electron beam irradiates the specimen through a pipe electrode positioned around the optical axis for preventing the deflection by the electric field generated by the scintillator and accelerating electrode. A mesh electrode is incorporated between said pipe electrode and its outer pipe-shaped electrode so that the secondary electrons emanating from the specimen is attracted toward the electron gun by the electric field generated by said mesh electrode maintained at positive potential and then accelerated toward the secondary electron detecting means by the electric field generated by said accelerating electrode.

THE DRAWINGS

The above mentioned and other objects and features of this invention will be described with reference to the accompanying drawings in which:

FIG. 1 is a schematic view of a conventional device for detecting secondary electrons, and FIGS. 2 and 3 are schematic views showing devices according to the present invention.

DESCRIPTION OF THE PREFERRED EMBODIMENT

Figure 1:
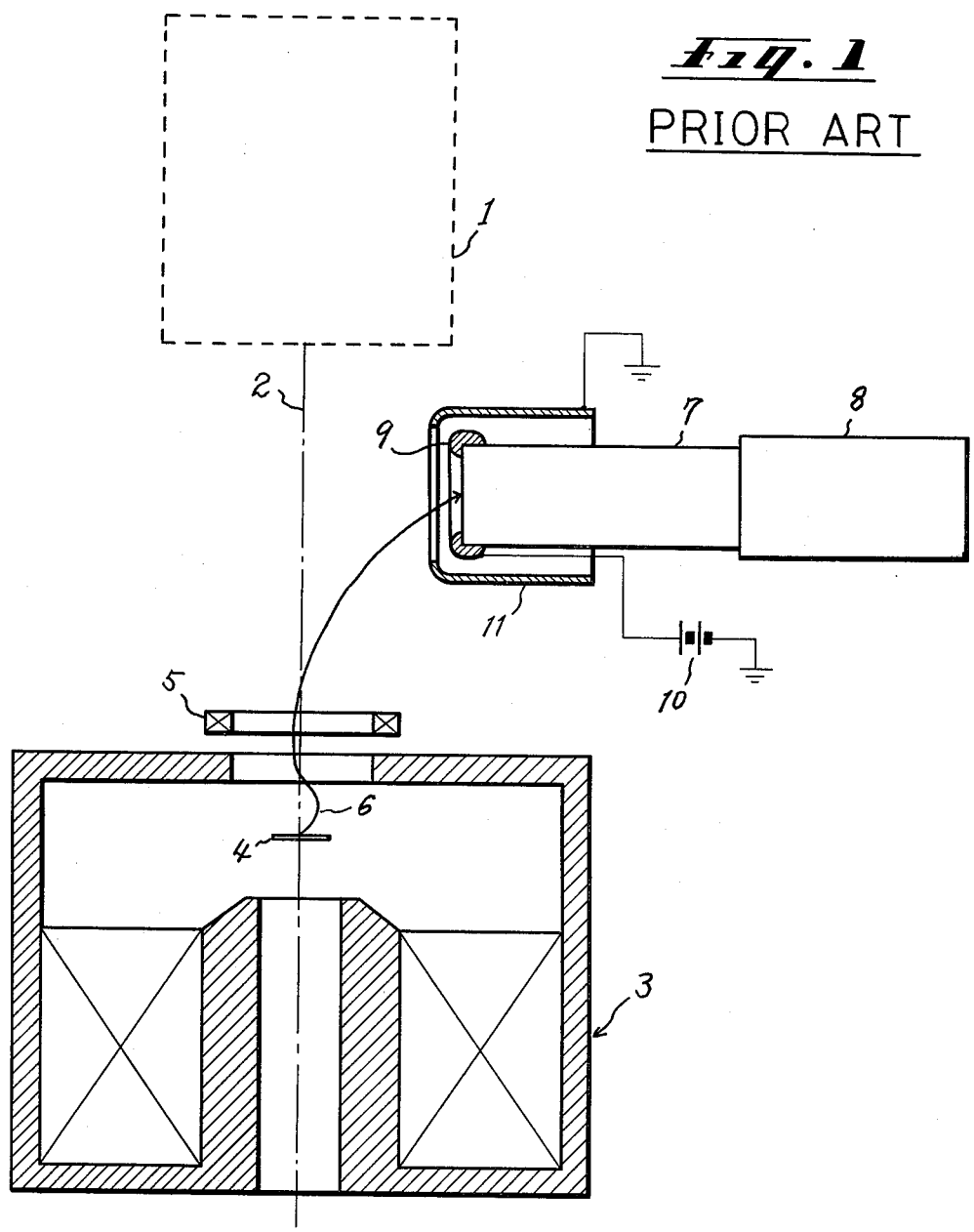

FIG. 2 shows one embodiment according to this invention. In FIG. 2, like reference numerals are used to denote like parts appearing in FIG. 1, and designated at 12 is a slender and electric conductive pipe electrode for preventing deflection of a primary electron beam accelerated with a low energy for irradiating a specimen. The pipe electrode 12 is maintained at ground potential and is surrounded by an outer pipe-shaped electrode 13. An annular-shaped mesh electrode 15 is attached between the pipe electrode 12 and the outer electrode 13 at a lower position thereof by means of an insulating ring 18. The output, for example approximately +500 V, of a d.c. power supply 14 is applied to the outer electrode 13 and mesh electrode 15. The outer pipe-shaped electrode 13 has a hole 13a toward which the front end of the detecting device faces. With this embodiment, even if the intensity of the objective lens magnetic field is not high enough to collect secondary electrons, the secondary electrons are attracted by an accelerating electric field generated by the mesh electrode 15 upwardly into a region where they are subjected to influence by an accelerating electric field by the accelerating ring electrode 9 and enter the scintillator. The primary electron beam, even if accelerated by a low voltage, is prevented from being deflected by the accelerating electric field by the accelerating ring electrode 9 since the pipe electrode 12 surrounds the path of the primary electron beam which is within the reach of the accelerating electric field.

According to the present invention, as described above, observation of scanning images produced by electron beams accelerated at low voltages can be effected without suffering prior difficulties. The present invention is not limited to the device according to the embodiment as illustrated in FIG. 2, but also is applicable to a device according to an embodiment of FIG. 3 for the same advantages.

FIG. 3 shows another embodiment according to this invention, whose structure is different from that of FIG. 2. A pipe electrode 16 and an outer pipe-shaped electrode 17 are kept at the same ground potential as that of the shield pipe 11 for the light pipe 7. An annular-shaped mesh electrode 20 extends between an insulating ring 18 attached to the pipe electrode 16 at a lower portion thereof and an insulating ring 19 attached to the outer pipe-shaped electrode 17 at a lower portion thereof. The mesh electrode 20 is held at a potential of the order of several hundred volts by a d.c. power supply 14 to collect secondary electrons from a specimen to the same advantage as that of the device of FIG. 2. According to this embodiment, a detector is laterally inserted in and fixed to the outer pipe-shaped electrode 17.

Having thus described the invention with the detail and particularity required by the Patent Laws, what is desired protected by Letters Patent is set forth in the following claims.

We claim:

1. In a device for detecting secondary electrons emanating from a specimen in a scanning electron microscope in which a primary electron beam emitted along an optical axis from an electron gun is directed onto said specimen placed substantially centrally in a gap between the magnetic pole pieces of an objective lens, said device comprising a scintillator with an accelerating electrode and a photomultipler that are located in a position displaced off the objective lens toward the electron gun, the improvement comprising a first pipe-shaped electrode disposed around the optical axis for preventing deflection of the primary electron beam due to the accelerating electrode associated with the scintillator, an annular-shaped mesh electrode supported from the first pipe electrode extending outwardly from the first pipe-shaped electrode and away from the optical axis, a second pipe-shaped electrode around the first supporting the peripheral edge of the mesh electrode, said mesh electrode maintained at a positive potential such that the mesh electrode and second pipe-shaped electrode guide the secondary electrons to the scintillator.

2. The improvement according to claim 2 comprising in that said first and second pipe-shaped electrodes are maintained at ground potential.

3. The improvement according to claim 1 comprising said second pipe-shaped electrode maintained at the same potential as that of said mesh electrode.

4. In a device for detecting secondary electrons emanating from a specimen in a scanning electron microscope in which a primary electron beam emitted along an optical axis from an electron gun is directed onto said specimen placed substantially centrally in a gap between the magnetic pole pieces of an objective lens, said device comprising a scintillator with an accelerating electrode and a photomultipler that are located in a position displaced off the objective lens toward the electron gun, the improvement comprising first and second coaxial pipe-shaped electrodes disposed about the optical axis, said pipe-shaped electrodes having a cylindrical axis substantially colinear with the electron optical axis and being positioned adjacent the accelerating electrode of the scintillator and an annular shaped mesh electrode disposed between the first and second electrodes near the axial ends of said electrodes nearest the specimen, said mesh electrode maintained at a potential such that the mesh electrode and second pipe-shaped electrode guide the secondary electrons to the scintillator.

5. The improvement according to claim 4 comprising in that said first and second pipe-shaped electrodes are maintained at ground potential.

6. The improvement according to claim 4 comprising said second pipe-shaped electrode maintained at the same potential as that of said mesh electrode.

* * * * *

UNITED STATES PATENT AND TRADEMARK OFFICE
CERTIFICATE OF CORRECTION

PATENT NO. : 4,442,355

DATED : April 10, 1984

INVENTOR(S) : Nobuaki Tamura et al.

It is certified that error appears in the above-identified patent and that said Letters Patent is hereby corrected as shown below:

Claim 1 - Column 3 Lines 49 & 50 "ena-mating" should read

--emanating--.

Signed and Sealed this

Fourteenth Day of August 1984

[SEAL]

Attest:

GERALD J. MOSSINGHOFF

Attesting Officer

Commissioner of Patents and Trademarks